US012788415B2

(12) United States Patent
He et al.

(10) Patent No.: US 12,788,415 B2
(45) Date of Patent: Nov. 10, 2026

(54) GRINDING DRILL WITH COOLING FUNCTION FOR MINIMALLY INVASIVE SPINAL SURGERY

(71) Applicant: BANGSHI MEDICAL TECHNOLOGY CO., LTD., Taizhou (CN)

(72) Inventors: Chengdong He, Taizhou (CN); Xin Yue, Taizhou (CN); Qingpeng Dong, Taizhou (CN)

(73) Assignee: BANGSHI MEDICAL TECHNOLOGY CO., LTD., Taizhou (CN)

( * ) Notice: Subject to any disclaimer, the term of this patent is extended or adjusted under 35 U.S.C. 154(b) by 196 days.

(21) Appl. No.: 18/857,227

(22) PCT Filed: Sep. 20, 2023

(86) PCT No.: PCT/CN2023/119934
§ 371 (c)(1),
(2) Date: Oct. 16, 2024

(87) PCT Pub. No.: WO2024/067279
PCT Pub. Date: Apr. 4, 2024

(65) Prior Publication Data

US 2025/0268609 A1 Aug. 28, 2025

(30) Foreign Application Priority Data

Sep. 30, 2022 (CN) ......................... 202222621844.0

(51) Int. Cl.
*A61B 17/16* (2006.01)

(52) U.S. Cl.
CPC ...... *A61B 17/1644* (2013.01); *A61B 17/1622* (2013.01); *A61B 17/1633* (2013.01);
(Continued)

(58) Field of Classification Search
CPC ............ A61B 17/1644; A61B 17/1622; A61B 17/1633; A61B 17/1671; A61B 2017/1651; A61B 2217/007
See application file for complete search history.

(56) References Cited

U.S. PATENT DOCUMENTS

| | | | | |
|---|---|---|---|---|
| 6,273,712 | B1 * | 8/2001 | Rach ........................ | A61D 5/00 433/116 |
| 2015/0201918 | A1 * | 7/2015 | Kumar ............... | A61B 17/1626 606/104 |
| 2017/0319217 | A1 * | 11/2017 | Manley .............. | A61B 17/1644 |

FOREIGN PATENT DOCUMENTS

| | | | |
|---|---|---|---|
| CN | 211243576 | U | 8/2020 |
| CN | 111973249 | A | 11/2020 |

(Continued)

*Primary Examiner* — Kevin T Truong
*Assistant Examiner* — Diana Jones
(74) *Attorney, Agent, or Firm* — Bayramoglu Law Offices LLC

(57) ABSTRACT

A grinding drill with a cooling function for a minimally invasive spinal surgery includes a grinder fixture, a grinding rod assembly, and a grinder. The grinder fixture includes a housing assembly and a sleeve located inside the housing assembly. One end of the grinding rod assembly extends into the housing assembly and is connected to the sleeve through a connecting shaft. An inner grinding rod is rotatably provided in the grinding rod assembly. The grinder runs through the other end of the grinding rod assembly and is connected to the inner grinding rod. An end of the inner grinding rod away from the grinder extends into the sleeve and is rotatably connected to the sleeve through a transmission element. A spiral cooling passage communicated with a water injection hole of the sleeve is provided between an inner wall of the housing assembly and an outer wall of the sleeve.

20 Claims, 4 Drawing Sheets

(52) U.S. Cl.
CPC .. *A61B 17/1671* (2013.01); *A61B 2017/1651* (2013.01); *A61B 2217/007* (2013.01)

(56) References Cited

FOREIGN PATENT DOCUMENTS

| | | | |
|---|---|---|---|
| CN | 212438753 | U | 2/2021 |
| CN | 214017702 | U | 8/2021 |
| CN | 215018430 | U | 12/2021 |
| CN | 218305024 | U | 1/2023 |
| CN | 219289589 | U | 7/2023 |
| CN | 219962985 | U | 11/2023 |

* cited by examiner

GRINDING DRILL WITH COOLING FUNCTION FOR MINIMALLY INVASIVE SPINAL SURGERY

CROSS REFERENCE TO THE RELATED APPLICATIONS

This application is the national phase entry of International Application No. PCT/CN2023/119934, filed on Sep. 20, 2023, which is based upon and claims priority to Chinese Patent Application No. 202222621844.0, filed on Sep. 30, 2022, the entire contents of which are incorporated herein by reference.

TECHNICAL FIELD

The present invention relates to the technical field of medical appliances, and in particular to a grinding drill with a cooling function for a minimally invasive spinal surgery.

BACKGROUND

The description of the background in the present application applies to related art of the present application, and is merely intended to illustrate the content of and facilitate understanding of the present application. It should not be deemed that the applicant clearly regards or is presumed to regard the description as belonging to the prior art of the present application on the filing date of the first application.

During spine grinding operations in surgical procedures, traditional manual grinders have problems such as low efficiency, inconvenience in observing the surgical site, and difficulty in controlling the force. As a result, it is difficult to remove a spine with low toughness around the surgical site, and it is easy to cause damage to a soft tissue with high toughness around, especially that adjacent to the spine, thereby affecting the recovery of the surgical site.

Traditional scrappers and grinding drills cannot meet the requirements of fine surgeries such as spine drilling due to their sizes. In addition, during high-speed rotation, external physiological saline needs to be introduced to cope with the heating problem of the grinding rod. The multi-instrument application has strict requirements for the surgical space due to the complexity of the spine area. However, the existing power system scrappers and grinding drills increase the surgical risk. For example, Chinese patent application CN211243576U discloses a grinding drill for a neurosurgery surgery. Mainly, a hollow tube is provided outside a grinding rod to introduce physiological saline for cooling. When in use, the external physiological saline needs to be continuously introduced. However, due to the limited surgical space of the spine, failure to timely extract the discharged physiological saline will seriously affect the surgical field of vision. Therefore, the existing power system scrappers and grinding drills are not suitable for drilling the spine.

At present, instrument cooling is still an urgent problem to be solved for spinal surgeries, especially those involving tissue scrapping and grinding.

SUMMARY

An objective of the present invention is to provide a grinding drill with a cooling function for a minimally invasive spinal surgery. The present invention solves the problems that the existing grinders for minimally invasive surgeries require a large amount of coolant and cannot effectively cool the grinding rod.

To solve the technical problems, the present invention adopts the following technical solution.

A grinding drill with a cooling function for a minimally invasive spinal surgery includes a grinder fixture, a grinding rod assembly, and a grinder, where the grinder fixture includes a housing assembly and a sleeve that is detachably connected inside the housing assembly; one end of the grinding rod assembly extends into the housing assembly and is connected to the sleeve through a connecting shaft; an inner grinding rod is rotatably provided in the grinding rod assembly; the grinder runs through the other end of the grinding rod assembly and is connected to the inner grinding rod; an end of the inner grinding rod away from the grinder extends into the sleeve and is rotatably connected to the sleeve through a transmission element; and the transmission element is connected to an external power handle through an interface of the sleeve; and a spiral cooling passage communicated with a water injection hole of the sleeve is provided between an inner wall of the housing assembly and an outer wall of the sleeve; the grinding rod assembly is provided with a water inlet; and the water inlet is communicated with the cooling passage through a chamber inside the housing assembly.

In the present invention, the transmission element is connected to the external power handle through the interface, and the external power handle drives the inner grinding rod and the grinder to rotate and drill the spine. The external power handle is provided with an inlet pipe. When the external power handle is inserted into the interface and connected to the transmission element, the inlet pipe of the external power handle is communicated with the water injection hole of the sleeve, and the cooling water is introduced into the cooling passage and the chamber through the water injection hole. The cooling water enters the grinding rod assembly through the water inlet and cools the grinding rod assembly and the inner grinding rod. The cooling water finally flows through the grinder from the grinding rod assembly to cool the grinder, thereby reducing thermal damage to the tissue during the grinding process.

Further, the grinding rod assembly includes a fourth outer tube, a third outer tube, a second outer tube and a first outer tube that are arranged sequentially from inside to outside; and the fourth outer tube, the third outer tube, the second outer tube and the first outer tube are sequentially communicated from outside to inside to form a cooling water passage for cooling the grinder and the inner grinding rod.

Further, a cavity is formed between each two adjacent outer tubes; the water inlet is located on an outer wall of an end of the first outer tube adjacent to the connecting shaft; a side wall of the second outer tube is provided with a water guide passage that is communicated with the cavity between the first outer tube and the second outer tube; the third outer tube is provided with a water guide hole that is communicated with the cavity between the second outer tube and the third outer tube; and an end of each of the fourth outer tube and the third outer tube adjacent to the grinder is provided with a water outlet that is communicated with the cavity.

In the present invention, the cooling water enters the cavity between the first outer tube and the second outer tube through the water inlet of the first outer tube, and enters the cavity between the second outer tube and the third outer tube through the water guide passage on the outer wall of the second outer tube. The cooling water enters the cavity between the third outer tube and the fourth outer tube through the water guide hole of the third outer tube, and finally flows towards the grinder through the water outlet passage to cool the grinder.

Further, the housing assembly includes a fastening element and a water-cooled housing that is detachably connected to the fastening element; the fourth outer tube, the third outer tube, the second outer tube, and the first outer tube all extend into the fastening element and are connected to the connecting shaft through the first outer tube; the chamber is a gap between the fastening element and the connecting shaft; and the cooling passage is located between an inner wall of the water-cooled housing and the outer wall of the sleeve.

In the present invention, the fastening element is configured to strengthen the connection between the grinding rod assembly and the water-cooled housing, thereby improving the connection stability between the grinding rod assembly and the grinder fixture.

Further, an end of the water-cooled housing away from the fastening element is clamped to a locking element configured to lock the external power handle.

In the present invention, when the interface of the sleeve is connected to the external power handle, the locking element locks the sleeve, the water-cooled housing, and the external power handle, thereby improving the connection stability.

Further, an outer wall of the inner grinding rod is wrapped by an anti-friction tube; and the fourth outer tube is located outside the anti-friction tube.

In the present invention, the anti-friction tube reduces the friction between the inner grinding rod and the fourth outer tube.

Further, a gap is formed between the fourth outer tube and the grinder.

The gap is designed to prevent an end position of the fourth outer tube adjacent to the grinder from being tangled by a tissue.

Further, the grinder is connected to the inner grinding rod through a steel tube; and an end of the grinder away from the inner grinding rod forms an emery spherical grinding head, conical grinding head, or grinding head with a cutting edge.

In the present invention, different grinders can be selected according to different surgical environments.

Further, the transmission element includes a bearing provided inside the sleeve and a coupling in a rotational fit with the bearing; the coupling is connected to the inner grinding rod; and the coupling is connected to the external power handle through the interface.

In the present invention, the inner grinding rod is connected to the coupling, and the coupling is connected to the external power handle through the interface. The external power handle is activated to drive the coupling to rotate around the bearing, thereby driving the inner grinding rod and the grinder to rotate for grinding operations.

Further, a sealing ring is provided between the connecting shaft and the sleeve.

In the present invention, the sealing ring is configured to connect the connecting shaft to the sleeve in a sealed manner, thereby preventing the cooling water from entering the connecting shaft to cause the impact on the rotation of the inner grinding rod.

Compared with the prior art, the present invention has the following beneficial effects:

1. In the present invention, the transmission element is connected to the external power handle through the interface, and the external power handle drives the inner grinding rod and the grinder to rotate and drill the spine. The inlet pipe of the external power handle is communicated with the water injection hole, and the cooling water is introduced into the cooling passage and the chamber through the water injection hole. The cooling water enters the grinding rod assembly through the water inlet and cools the grinding rod assembly and the inner grinding rod. The cooling water finally flows through the grinder from the grinding rod assembly to cool the grinder, thereby reducing thermal damage to the tissue during the grinding process.
2. In the present invention, the coaxial multi-tube structure of the grinding rod assembly reduces the amount of the cooling water and undertakes the delivery of the cooling water in the grinder fixture, replacing a traditional external cooling pipe. The present invention realizes cooling of the high-speed grinding drill, improves the utilization of the space in surgeries of complex cavities, and accelerates the surgical process.

Figure 1:
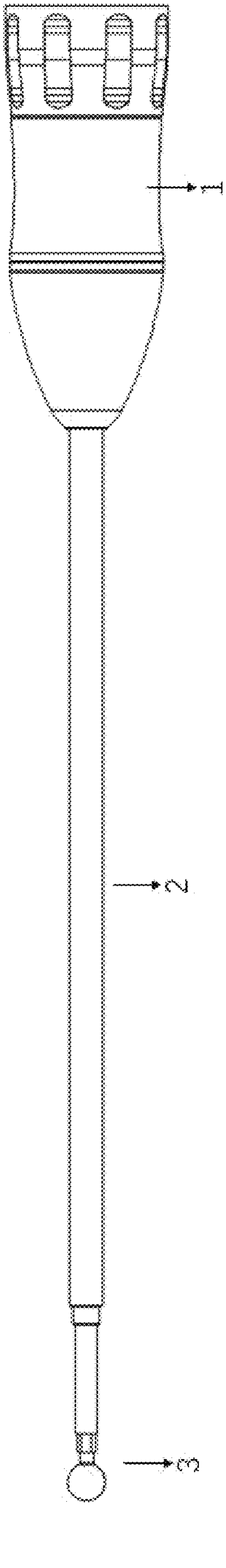
FIG. 1 is a structural diagram of a grinding drill with a cooling function according to the present invention.
Figure 2:
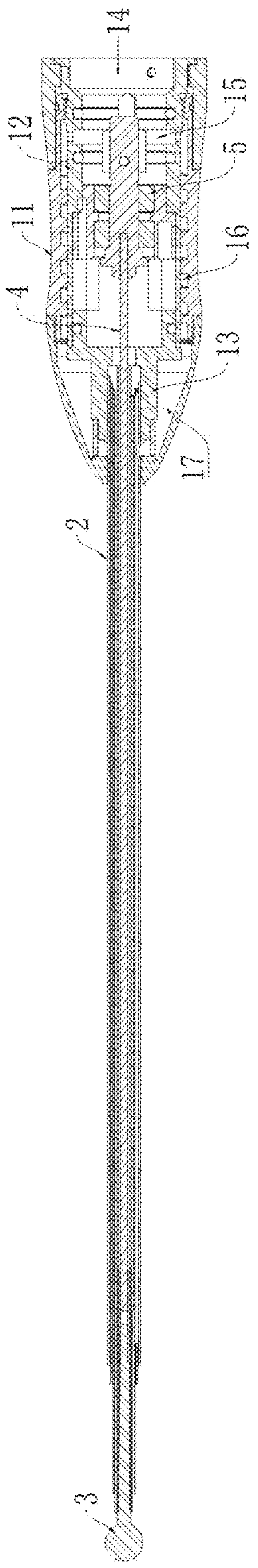
FIG. 2 is a section view of the grinding drill with the cooling function according to the present invention.

Reference Numerals: 1. grinder fixture; 11. housing assembly; 111. fastening element; 112. water-cooled housing; 113. locking element; 12. sleeve; 13. connecting shaft; 131. sealing ring; 14. interface; 15. water inlet; 16. cooling passage; 17. chamber; 2. grinding rod assembly; 21. water inlet; 22. fourth outer tube; 23. third outer tube; 231. water guide hole; 24. second outer tube; 241. water guide passage; 25. first outer tube; 26. water outlet; 3. grinder; 31. steel tube; 4. inner grinding rod; 5. transmission element; 51. bearing; 52. coupling; and 6. anti-friction tube.

DETAILED DESCRIPTION OF THE EMBODIMENTS

The technical solutions of the present invention are clearly and completely described with reference to the drawings. Apparently, the described embodiments are merely some rather than all of the embodiments of the present invention. All other embodiments obtained by those having ordinary skill in the art based on the embodiments of the present invention without creative efforts shall fall within the protection scope of the present invention.

As shown in FIGS. 1 to 4, a grinding drill with a cooling function for a minimally invasive spinal surgery includes grinder fixture 1, grinding rod assembly 2, and grinder 3. The grinder fixture 1 includes housing assembly 11 and sleeve 12 that is detachably connected inside the housing assembly 11. An outer wall of the sleeve 12 is provided with an external thread. A corresponding position of water-cooled housing 112 in the housing assembly 11 is provided with an internal thread that matches the external thread to achieve a detachable connection. One end of the grinding rod assembly 2 extends into the housing assembly 11 and is connected to the sleeve 12 through connecting shaft 13. Sealing ring 131 is provided between the connecting shaft 13 and the sleeve 12. Specifically, an end of the connecting shaft 13 away from the grinding rod assembly 2 is embedded into the sleeve 12. An outer wall of the connecting shaft 13 is provided with a circular groove, and the circular groove is configured to accommodate the sealing ring 131, such that the sleeve 12 and the connecting shaft 13 are in a sealed state to prevent cooling water from entering into the sleeve 12 to interfere with transmission element 5.

Inner grinding rod 4 is rotatably provided in the grinding rod assembly 2. The grinder 3 runs through the other end of the grinding rod assembly 2 and is connected to the inner grinding rod 4. An end of the inner grinding rod 4 away from the grinder 3 extends into the sleeve 12 and is rotatably connected to the sleeve 12 through the transmission element 5. The transmission element 5 is connected to an external power handle through interface 14 of the sleeve 12. The transmission element 5 includes bearing 51 provided inside the sleeve 12 and coupling 52 in a rotational fit with the bearing 51. The coupling 52 is connected to the inner grinding rod 4, and the coupling 52 is connected to the external power handle through the interface 14. The external power handle is a driving component of an external host system. The external power handle drives the coupling 52 to rotate around the bearing 51, which in turn drives the inner grinding rod 4 and the grinder 3 to rotate and drill a spine.

Spiral cooling passage 16 communicated with water injection hole 15 of the sleeve 12 is provided between an inner wall of the housing assembly 11 and the outer wall of the sleeve 12. The external power handle is inserted into the interface 14 to connect the coupling 52. A water inlet pipe of the external power handle is inserted into the water injection hole 15 so as to introduce the cooling water into the water injection hole 15. The grinding rod assembly 2 is provided with water inlet 21. The water inlet 21 is communicated with the cooling passage 16 through chamber 17 inside the housing assembly 11. The cooling water enters the cooling passage 16 from the water injection hole 15, flows through the chamber 17, and flows into the grinding rod assembly 2 from the water inlet 21 to cool the grinding rod assembly 2, the inner grinding rod 4, and the grinder 3, thereby reducing thermal damage to the tissue during the grinding process.

Figure 4:
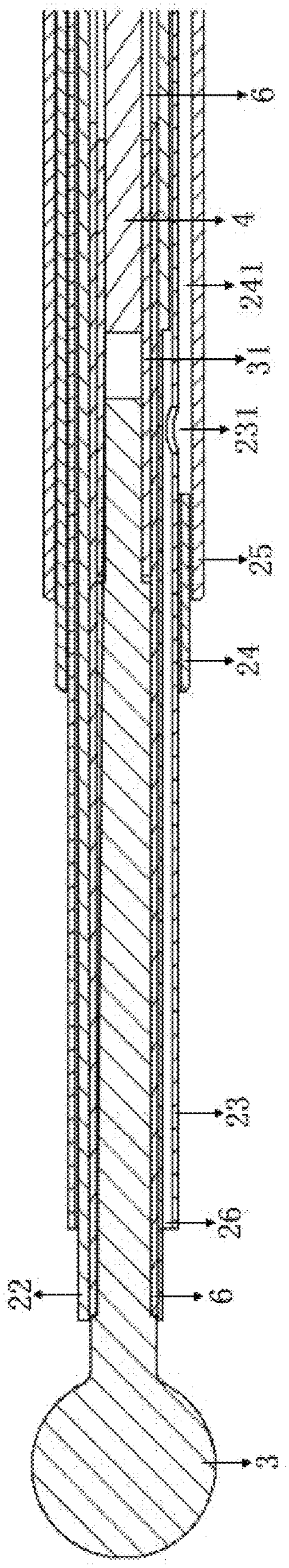
FIG. 4 is a structural diagram of a grinding rod assembly, an inner grinding rod, and a grinder.

As shown in FIG. 4, the grinding rod assembly 2 includes fourth outer tube 22, third outer tube 23, second outer tube 24 and first outer tube 25 that are arranged sequentially from inside to outside. The fourth outer tube 22, the third outer tube 23, the second outer tube 24 and the first outer tube 25 are sequentially communicated from outside to inside to form a cooling water passage for cooling the grinder 3 and the inner grinding rod 4. A cavity is formed between each two adjacent outer tubes. The water inlet 21 is located on an outer wall of an end of the first outer tube 25 adjacent to the connecting shaft 13. A side wall of the second outer tube 24 is provided with water guide passage 241 that is communicated with the cavity between the first outer tube 25 and the second outer tube 24. The third outer tube 23 is provided with water guide hole 231 that is communicated with the cavity between the second outer tube 24 and the third outer tube 23. An end of each of the fourth outer tube 22 and the third outer tube 23 adjacent to the grinder 3 is provided with water outlet 26 that is communicated with the cavity.

The cooling water enters the cavity between the first outer tube 25 and the second outer tube 24 through the water inlet 21. The cooling water inside the cavity between the first outer tube 25 and the second outer tube 24 enters the cavity between the second outer tube 24 and the third outer tube 23 through the water guide passage 241. The cooling water in the cavity between the second outer tube 24 and the third outer tube 23 is guided into the cavity between the fourth outer tube 22 and the third outer tube 23 through the water guide hole 231, and finally reaches the grinder 3 from the water outlet 26. In this embodiment, the cooling water is medical sterile physiological saline. The cooling water passage for cooling the grinder 3 and the inner grinding rod 4 is formed by the cavity between the first outer tube 25 and the second outer tube, the water guide passage 241, the cavity between the second outer tube 24 and the third outer tube 23, the water guide hole 231, the cavity between the third outer tube 23 and the fourth outer tube 22, and the water outlet 26.

Preferably, a gap is formed between the fourth outer tube 22 and the grinder 3, and the gap is provided to prevent an end position of the fourth outer tube 22 adjacent to the grinder 3 from being tangled by a tissue.

Figure 3:
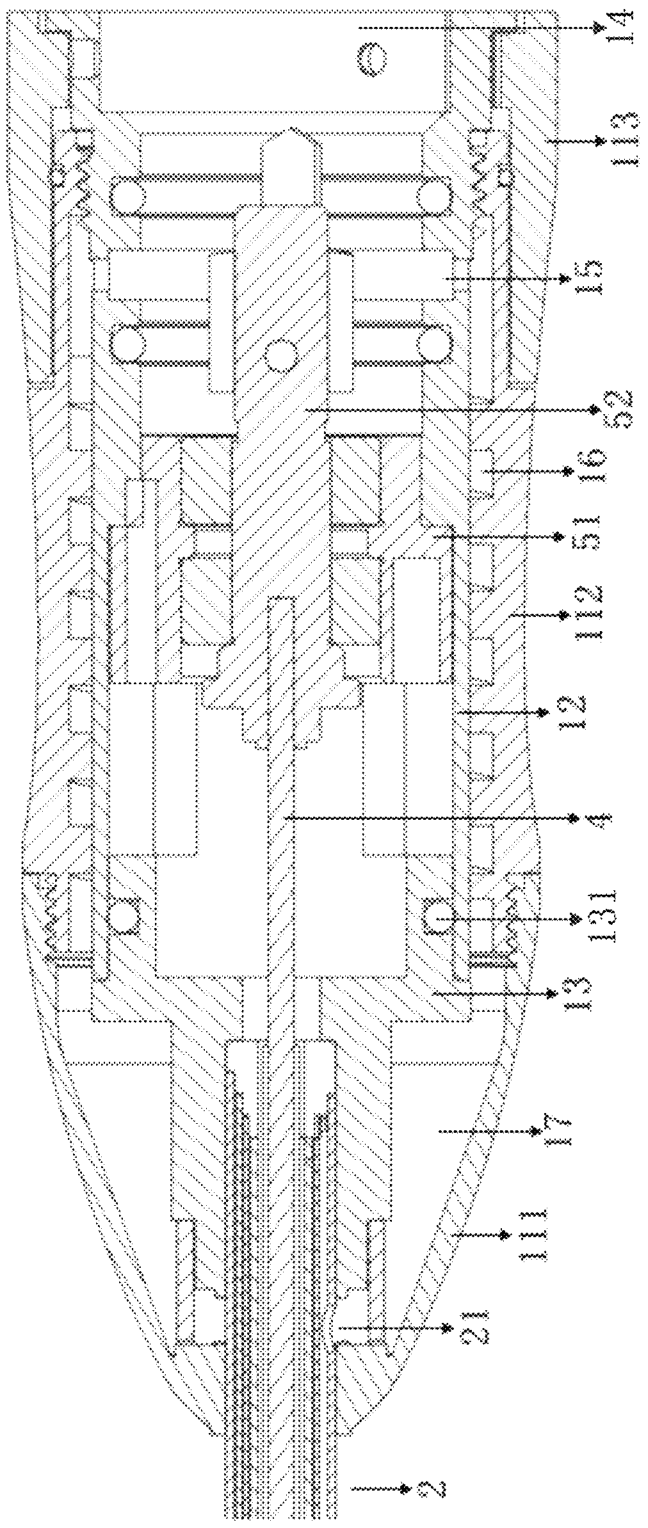
FIG. 3 is a specific structural diagram of a grinder fixture.

As shown in FIG. 3, the housing assembly 11 includes fastening element 111 and the water-cooled housing 112 that is detachably connected to the fastening element 111. The fastening element 111 is configured to strengthen the connection stability between the grinding rod assembly 2 and the grinder fixture 1. An inner wall of an end of the fastening element 111 adjacent to the water-cooled housing 112 is provided with an internal thread, and a corresponding position of the water-cooled housing 112 is provided with an external thread that matches the internal thread, thereby achieving a detachable connection. The fourth outer tube 22, the third outer tube 23, the second outer tube 24, and the first outer tube 25 all extend into the fastening element 111 and are connected to the connecting shaft 13 through the first outer tube 25. The chamber 17 is a gap between the fastening element 111 and the connecting shaft 13. The cooling passage 16 is located between an inner wall of the water-cooled housing 112 and the outer wall of the sleeve 12.

An end of the water-cooled housing 112 away from the fastening element 111 is clamped to locking element 113 configured to lock the external power handle. An outer wall of the end of the water-cooled housing 112 away from the fastening element 111 is provided with a clamping groove. An inner wall of the locking element 113 is correspondingly provided with a circular protrusion that matches the clamping groove, thereby achieving a clamping purpose. The locking element 113 clamps the sleeve 12, the water-cooled housing 112, and the external power handle to improve the connection stability. The locking element 113 is provided with a plurality of through holes for an inlet pipe of the external power handle to pass through.

In order to reduce the friction between the fourth outer tube 22 and the inner grinding rod 4, an outer wall of the inner grinding rod 4 is wrapped by anti-friction tube 6. The fourth outer tube 22 is located outside the anti-friction tube 6. The anti-friction tube 6 is made of an existing polytetrafluoroethylene tube, and the polytetrafluoroethylene tube has the properties such as high temperature resistance, friction resistance, and corrosion resistance.

As shown in FIG. 4, the grinder 3 is connected to the inner grinding rod 4 through steel tube 31. An end of the grinder 3 away from the inner grinding rod 4 forms an emery spherical grinding head, conical grinding head, or grinding head with a cutting edge. Different grinders can be selected according to different surgical environments.

In the present invention, when in use, the external power handle is inserted into the interface 14 and connected to the coupling 52. The external power handle drives the inner grinding rod 4 and the grinder 3 to rotate and drill the spine. The inlet pipe of the external power handle passes through the through holes of the locking element 113 and is communicated with the water injection hole 15. The cooling water introduced by the water injection hole 15 further enters the grinding rod assembly 2 through the cooling passage 16, the chamber 17, and the water inlet 21. The coaxial multi-tube structure of the grinding rod assembly 2 increases the flow time of the cooling water, allowing for full contact between the cooling water and the grinding rod assembly 2. Compared with a traditional external cooling pipe, in the present invention, the amount of the cooling water used by the grinding rod assembly 2 within the same time is reduced, and the cooling water can fully contact the grinding rod assembly 2, thereby effectively cooling the grinding rod assembly 2 and the inner grinding rod 4 and further cooling the grinder 3, so as to achieve cooling of the high-speed grinding drill. The present invention improves the utilization of the space in complex surgeries and accelerates the surgical process.

The above described are merely preferred embodiments of the present invention, and are not intended to limit the present invention. Any modification, equivalent substitute and improvement without departing from the spirit and principle of the present invention shall be included within the protection scope of the present invention.

What is claimed is:

1. A grinding drill with a cooling function for a minimally invasive spinal surgery, comprising a grinder fixture, a grinding rod assembly, and a grinder, wherein the grinder fixture comprises a housing assembly and a sleeve, wherein the sleeve is detachably connected inside the housing assembly; a first end of the grinding rod assembly extends into the housing assembly and is connected to the sleeve through a connecting shaft; an inner grinding rod is rotatably provided in the grinding rod assembly; the grinder runs through a second end of the grinding rod assembly and is connected to the inner grinding rod; an end of the inner grinding rod away from the grinder extends into the sleeve and is rotatably connected to the sleeve through a transmission element; and the transmission element is connected to an external power handle through an interface of the sleeve; and a spiral cooling passage communicated with a water injection hole of the sleeve is provided between an inner wall of the housing assembly and an outer wall of the sleeve; the grinding rod assembly is provided with a water inlet; and the water inlet is communicated with the spiral cooling passage through a chamber inside the housing assembly.

2. The grinding drill with the cooling function for the minimally invasive spinal surgery according to claim 1, wherein the grinding rod assembly comprises a fourth outer tube, a third outer tube, a second outer tube and a first outer tube, wherein the fourth outer tube, the third outer tube, the second outer tube and the first outer tube are arranged sequentially from inside to outside; and the fourth outer tube, the third outer tube, the second outer tube and the first outer tube are sequentially communicated from outside to inside to form a cooling water passage for cooling the grinder and the inner grinding rod.

3. The grinding drill with the cooling function for the minimally invasive spinal surgery according to claim 2, wherein a cavity is formed between each two adjacent outer tubes; the water inlet is located on an outer wall of an end of the first outer tube adjacent to the connecting shaft; a side wall of the second outer tube is provided with a water guide passage, wherein the water guide passage is communicated with the cavity between the first outer tube and the second outer tube; the third outer tube is provided with a water guide hole, wherein the water guide hole is communicated with the cavity between the second outer tube and the third outer tube; and an end of each of the fourth outer tube and the third outer tube adjacent to the grinder is provided with a water outlet, wherein the water outlet is communicated with the cavity.

4. The grinding drill with the cooling function for the minimally invasive spinal surgery according to claim 3, wherein the grinder is connected to the inner grinding rod through a steel tube; and an end of the grinder away from the inner grinding rod forms an emery spherical grinding head, conical grinding head, or grinding head with a cutting edge.

5. The grinding drill with the cooling function for the minimally invasive spinal surgery according to claim 4, wherein the transmission element comprises a bearing provided inside the sleeve and a coupling in a rotational fit with the bearing; the coupling is connected to the inner grinding rod; and the coupling is connected to the external power handle through the interface.

6. The grinding drill with the cooling function for the minimally invasive spinal surgery according to claim 2, wherein the housing assembly comprises a fastening element and a water-cooled housing, wherein the water-cooled housing is detachably connected to the fastening element; the fourth outer tube, the third outer tube, the second outer tube, and the first outer tube all extend into the fastening element and are connected to the connecting shaft through the first outer tube; the chamber is a gap between the fastening element and the connecting shaft; and the spiral cooling passage is located between an inner wall of the water-cooled housing and the outer wall of the sleeve.

7. The grinding drill with the cooling function for the minimally invasive spinal surgery according to claim 6, wherein an end of the water-cooled housing away from the fastening element is clamped to a locking element configured to lock the external power handle.

8. The grinding drill with the cooling function for the minimally invasive spinal surgery according to claim 7, wherein the grinder is connected to the inner grinding rod through a steel tube; and an end of the grinder away from the inner grinding rod forms an emery spherical grinding head, conical grinding head, or grinding head with a cutting edge.

9. The grinding drill with the cooling function for the minimally invasive spinal surgery according to claim 8, wherein the transmission element comprises a bearing provided inside the sleeve and a coupling in a rotational fit with the bearing; the coupling is connected to the inner grinding rod; and the coupling is connected to the external power handle through the interface.

10. The grinding drill with the cooling function for the minimally invasive spinal surgery according to claim 6, wherein a gap is formed between the fourth outer tube and the grinder.

11. The grinding drill with the cooling function for the minimally invasive spinal surgery according to claim 10, wherein the grinder is connected to the inner grinding rod through a steel tube; and an end of the grinder away from the inner grinding rod forms an emery spherical grinding head, conical grinding head, or grinding head with a cutting edge.

12. The grinding drill with the cooling function for the minimally invasive spinal surgery according to claim 11, wherein the transmission element comprises a bearing provided inside the sleeve and a coupling in a rotational fit with the bearing; the coupling is connected to the inner grinding rod; and the coupling is connected to the external power handle through the interface.

13. The grinding drill with the cooling function for the minimally invasive spinal surgery according to claim 6, wherein the grinder is connected to the inner grinding rod through a steel tube; and an end of the grinder away from the inner grinding rod forms an emery spherical grinding head, conical grinding head, or grinding head with a cutting edge.

14. The grinding drill with the cooling function for the minimally invasive spinal surgery according to claim 13, wherein the transmission element comprises a bearing provided inside the sleeve and a coupling in a rotational fit with the bearing; the coupling is connected to the inner grinding rod; and the coupling is connected to the external power handle through the interface.

15. The grinding drill with the cooling function for the minimally invasive spinal surgery according to claim 2, wherein an outer wall of the inner grinding rod is wrapped by an anti-friction tube; and the fourth outer tube is located outside the anti-friction tube.

16. The grinding drill with the cooling function for the minimally invasive spinal surgery according to claim 15, wherein the grinder is connected to the inner grinding rod through a steel tube; and an end of the grinder away from the inner grinding rod forms an emery spherical grinding head, conical grinding head, or grinding head with a cutting edge.

17. The grinding drill with the cooling function for the minimally invasive spinal surgery according to claim 16, wherein the transmission element comprises a bearing provided inside the sleeve and a coupling in a rotational fit with the bearing; the coupling is connected to the inner grinding rod; and the coupling is connected to the external power handle through the interface.

18. The grinding drill with the cooling function for the minimally invasive spinal surgery according to claim 2, wherein the grinder is connected to the inner grinding rod through a steel tube; and an end of the grinder away from the inner grinding rod forms an emery spherical grinding head, conical grinding head, or grinding head with a cutting edge.

19. The grinding drill with the cooling function for the minimally invasive spinal surgery according to claim 18, wherein the transmission element comprises a bearing provided inside the sleeve and a coupling in a rotational fit with the bearing; the coupling is connected to the inner grinding rod; and the coupling is connected to the external power handle through the interface.

20. The grinding drill with the cooling function for the minimally invasive spinal surgery according to claim 18, wherein a sealing ring is provided between the connecting shaft and the sleeve.

* * * * *